United States Patent [19]
Blackburne et al.

[11] 4,093,711
[45] June 6, 1978

[54] ORAL HYGIENE

[75] Inventors: Owen Rodney Blackburne, Baltimore; Warren B. Shapiro, Randallstown, both of Md.

[73] Assignee: Noxell Corporation, Baltimore, Md.

[21] Appl. No.: 714,149

[22] Filed: Aug. 13, 1976

[51] Int. Cl.² .............................................. N61K 7/22
[52] U.S. Cl. ........................................ 424/54; 424/49; 260/404.5
[58] Field of Search ............. 260/398, 404.5 R, 404.5; 544/351; 424/49-54

[56] References Cited

U.S. PATENT DOCUMENTS 3,206,512  9/1965  Koebner et al. ............... 260/404.5 R

OTHER PUBLICATIONS

L'Orange et al, "Composition for . . . protheses", Chem Abst. vol. 84, 1976, parag. 184919v.
Jungumann et al., "Fatty Amine Oxides".

*Primary Examiner*—Natalie Trousof
*Assistant Examiner*—Cary Owens
*Attorney, Agent, or Firm*—Pollock, Vande Sande & Priddy

[57] ABSTRACT

Method for retarding pellicle and plaque formation which includes contacting sites of plaque formation and growth with dental preparation containing certain amine oxide compounds and dental preparations containing the amine oxide compounds.

35 Claims, No Drawings

ORAL HYGIENE

BACKGROUND OF THE INVENTION

The present invention relates to a method for retarding pellicle and plaque formation and dental preparations employed for such purposes. More specifically, the present invention relates to a method for retarding pellicle and plaque formation by contacting sites of plaque formation and growth (e.g., the oral cavity) with certain amine oxide compounds and dental preparations containing the amine oxide compounds.

Dental pellicle is a soft deposit tenaciously held on the surfaces of the teeth which includes salivary protein. Dental plaque is a product of microbial growth, is tenaciously attached to the surfaces of the teeth and adjacent gingiva, and exhibits a definite microscopic structure. If not removed, the plaque will become mineralized to form calculus and eventually lead to dental caries. Dental experts generally believe that calculus, also known as tartar, is dental plaque which has become mineralized with calcium phosphate, magnesium phosphate, calcium carbonate and other trace minerals found in the mouth. If calculus is not removed from around teeth and under the gum, inflammation can result which can ultimately lead to periodontal disease and subsequent tooth loss.

Although plaque can be removed from the teeth by thorough abrasive action, it quickly reforms on the tooth surfaces. Accordingly, the incidence of dental calculus and subsequent periodontal disease can be reduced by reducing or preventing the deposition of plaque and by means which prevent mineralization of the plaque.

It is therefore an object of the present invention to provide a method for retarding pellicle and plaque formation, and to provide compositions containing active ingredients which retard pellicle and plaque deposition. Another object of the present invention is to provide non-toxic dentifrice preparations for retarding pellicle and plaque formation. The dentifrice preparations include toothpastes, dental creams, tooth powders, mouthwashes, lozenges, tablets, aerosol sprays, chewing gum, toothpicks, dental floss, denture cleansers, and the like.

SUMMARY OF THE INVENTION

One aspect of the present invention is a method for retarding pellicle and plaque deposition which comprises intermittently contacting sites of plaque formation and growth with a preparation comprising, in an amount sufficient to retard pellicle and plaque formation, a compound of the formula:

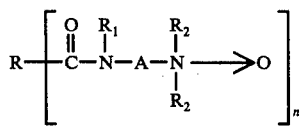

(1)

wherein R is a monovalent or divalent hydrocarbyl group containing at least 13 carbon atoms, $n$ is one when R is monovalent and is 2 when R is divalent; $R_1$ is H or an alkyl group containing from 1 to about 3 carbon atoms; A is a divalent hydrocarbon bridge containing from 1 to about 6 carbon atoms; and each $R_2$ individually is an alkyl group containing from 1 to about 5 carbon atoms; or both $R_2$ groups are interconnected to form a heterocyclic ring with the N atom to which they are attached and containing 5 to 6 members in the ring.

The present invention is also concerned with certain dentifrice preparations containing an amount sufficient to retard pellicle and plaque formation of a compound of formula (1) above.

DESCRIPTION OF PREFERRED EMBODIMENTS

The objectives of the present invention are accomplished by dental preparations which contain a compound of the formula:

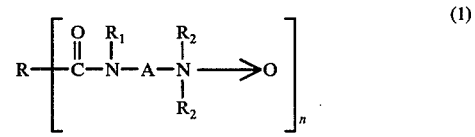

(1)

wherein R in the above formula is a hydrocarbyl group containing at least 13 carbon atoms. R usually contains no more than about 21 carbon atoms, and preferably from 15 to about 21 carbon atoms; and most preferably from 15 to about 17 carbon atoms. Examples of some suitable hydrocarbyl groups include aliphatic hydrocarbon groups; alkaryl groups; aralkyl groups; alkacycloalkyl groups; and cycloalkalkyl groups. The preferred hydrocarbyl group is aliphatic hydrocarbon group. The aliphatic hydrocarbon group can be saturated or can be ethylenically unsaturated and can be straight chain or branched chain. Examples of some suitable aliphatic hydrocarbon groups include tridecyl, pentadecyl, heptadecyl, tetradecyl, and heptadecenyl. The aryl portion of the alkaryl and aralkyl groups include phenyl and naphthyl. The cycloalkyl portion of the alkacycloalkyl and cycloalkalkyl groups include cyclopropyl, cyclobutyl, cyclopentyl, and cyclohexyl. R can be monovalent or divalent and is preferably monovalent. When R is monovalent, $n$ is 1 and when R is divalent $n$ is 2.

$R_1$ is hydrogen or an alkyl group containing from 1 to about 3 carbon atoms such as methyl, ethyl and propyl. $R_1$ is preferably hydrogen or methyl and most preferably is hydrogen.

A is a divalent hydrocarbon bridge containing from 1 to about 6 carbon atoms. A can be straight chain or branched chain and includes alkylene groups, alkylidene groups, cycloalkylene groups, and arylene groups. Examples of some suitable alkylene groups include methylene, ethylene, propylene, butylene, pentylene and hexylene. Examples of some suitable alkylidene groups include ethylidene and isopropylidene. Examples of cycloalkylene groups include cyclopropylene, cyclobutylene, cyclopentylene, and cyclohexylene. An example of an arylene group is phenylene. Preferably A is an alkylene or alkylidene group. Most preferably A is an alkylene or alkylidene group containing 1 to 3 carbon atoms.

Each $R_2$ individually is an alkyl group containing from 1 to about 5 carbon atoms; or both $R_2$ groups are interconnected to form a heterocyclic ring with the N atom to which they are attached and containing 5 to 6 members in the ring. Examples of some heterocyclic rings include morpholinyl, piperidinyl, pyrrolidinyl, and piperazinyl. Preferably $R_2$ is an alkyl group. The alkyl group preferably contains 1 to 3 carbon atoms.

The preferred compounds employed in the present invention have the following structural formula:

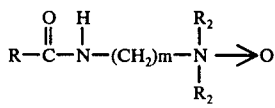 (2)

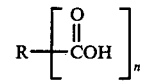 (4)

to provide an amido amine of the formula:

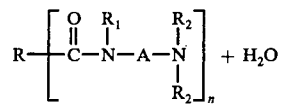 (5)

wherein R is an aliphatic hydrocarbon group containing at least 13 carbon atoms; $m$ is a whole number integer from 1 to 3; and $R_2$ individually is an alkyl group containing 1 to 3 carbon atoms.

Examples of some specific compounds suitable for the present invention include dimethylaminopropyl stearamide N-oxide; dimethylaminopropyl tallow amide N-oxide; diethylaminopropylpalmitamide N-oxide; dimethylaminopropylmyristamide N-oxide; dimethylaminopropylpentadecanamide N-oxide; dimethylaminopropyloleamide N-oxide; and dimethylaminopropylpalmitamide N-oxide.

It has been observed that compounds similar to those employed according to the present invention, except that R contains less than 13 carbon atoms, do not retard plaque and pellicle deposition as achieved by the present invention. For instance, it has been observed that compositions of about 10% by weight of dimethylaminopropyl cocoamide N-oxide (Ammonyx CDO from Onyx Chemical) and the remainder distilled water does not provide plaque inhibition activity. Ammonyx CDO has the general structure described above in formula (2) except that

is from a coconut fatty acid which presumably includes minor amounts of fatty acids having 14 carbon atoms or more. However, in view of the small quantities of R groups having at least 13 carbon atoms in Ammonyl CDO, the concentration of compounds of the type falling within the scope of this invention, when Ammonyx CDO is further diluted to concentrations found suitable for amine oxides within the scope of the present invention, are apparently not sufficient to retard the formation of plaque and pellicle. However, undiluted Ammonyx CDO contains sufficient quantities of amine oxides within the scope of the present invention to be effective against plaque and pellicle formation.

Various of the compounds suitable for the present invention are available. For instance, dimethylaminopropyl tallow amide N-oxide is available under the trade designation Tegamine HTG oxide from Inolex, and dimethylaminopropylpalmitamide N-oxide is available under the trade designation Tegamine P Oxide from Inolex.

The compounds suitable for the present invention can be prepared, for instance, by reacting a diamine of the formula:

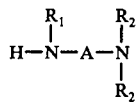 (3)

with a mono- or dicarboxylic acid of the formula:

The progress of this reaction can be readily monitored by measuring the amount of water formed. When a monocarboxylic acid is employed, the acid and amine are used in about equimolar quantities. When a dicarboxylic acid is employed, the molar ratio of acid to amine is about 1:2. After the amidoamine is isolated from the reaction mixture, it is reacted with an oxidizing agent such as hydrogen peroxide according to the following reaction which shows hydrogen peroxide as an exemplary reactant for convenience to provide the compounds employed according to the present invention.

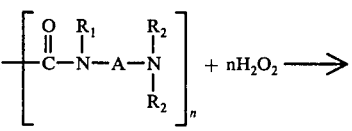

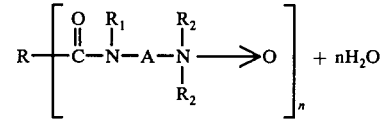

This latter reaction can be carried out under reflux for convenience when desired. The meanings of R, $R_1$, $R_2$, $n$, and A are the same as discussed hereinabove.

Examples of some diamines of formula (3) include 3-dimethylaminopropylamine, para-aminodiethylaniline; para-aminodimethylaniline; N-aminoethylpiperazine; N-aminopropylmorpholine; 3-diethylaminopropylamine; 3-ethylmethylaminopropylamine; and dimethylaminomethylamine.

Examples of some carboxylic acids of formula (4) include stearic acid; behenic acid; isostearic acid; palmitic acid; oleic acid; linoleic acid; linolenic acid, erucic acid, pentadecanoic acid, myristic acid, and tallow acids.

The amido amine oxide compounds employed according to the present invention are intermittently contacted with sites of plaque formation and growth such as the oral cavity in the form of a dental preparation. The amido amine oxides can be utilized to retard pellicle and plaque formation on dentures by soaking dentures in a suitable preparation. Accordingly, sites of plaque formation and growth as used herein refer to the oral cavity as well as dentures or false teeth while located in or out of the oral cavity.

The term "dental preparation" which is used herein is intended to designate products which in the ordinary course of usage are retained in contact with sites for plaque formation and growth such as in the human oral cavity for a time sufficient to contact substantially all of the dental surfaces but are not intentionally ingested.

When the amine oxide compounds are to be utilized in the oral cavity, such compounds are provided in a non-toxic carrier suitable for use in the oral cavity. For example, the amine oxide compounds can be dispersed in water and used as such. Some preparations to which the present invention are directed include toothpastes, dental creams, tooth powders, mouth rinses, lozenges, tablets, aerosol sprays, chewing gum, dental floss, dental toothpicks, and denture cleansers. The amount of the amine oxide employed according to the present invention is at least sufficient to provide a composition which retards pellicle and plaque formation and is generally at least about 0.1% by weight and preferably at least about 1% by weight of the amine oxide compound in the dental preparation. The maximum amount of amine oxide compound is dependent primarily upon economical and practical considerations and is generally about 25% by weight in the dental preparation.

In addition, the threshold effective amount of any amidoamine oxide compound is not only dependent upon the absolute quantity of the amidoamine oxide compound in the preparation but may also be dependent somewhat upon the amount of the amidoamine oxide compound relative to other constituents in the particular preparation, and the type of other constituents in the particular preparation. For instance, if the preparation contains an ingredient which interacts with the amidoamine oxide to render it inactive, it is apparent that the amount of the amidoamine oxide must be in excess of that which is interacted. Furthermore, the degree of rinsing after a treatment may have some effect upon the amount necessary. For instance, little or no rinsing may result in some buildup of the compound on the teeth which would reduce the amount needed in subsequent treatments. The minimum amount of the amidoamine oxide compound required for any particular preparation is readily ascertainable without undue experimentation.

When preparing dental preparations according to the present invention and particularly for application in the oral cavity, carriers and other additives suitable for the oral cavity and which are compatible with the amidoamine oxide and each other such as, for example, sudsing agents, flavoring agents, abrasive polishing compounds, humectants, and sweetening agents can be employed. The amount and type of these additive materials used can be varied greatly. In addition, the pH of dental preparations employed according to the present invention and particularly those for use in the oral cavity is usually between about 3 and about 9, and preferably between about 5 and about 7.5. The additives and pH for denture preparations not to be used in the oral cavity need not be suitable for the oral cavity.

Examples of some suitable water-insoluble abrasive polishing agents include dicalcium phosphate, hydrated aluminum oxide, calcium carbonate, calcium polymetaphosphate, dicalcium orthophosphate dihydrate, sodium polymetaphosphate, and various resinous abrasive materials such as particulate polyethylene, melamines, phenolics, ureas, melamine-ureas, melamine-formaldehydes, urea-formaldehydes, melamine-urea-formaldehydes, and cross-linked polyesters. Mixtures of abrasive polishing agents can be employed when desired.

The total amount of abrasive agent, when present, can range from about 0.5 to about 95% by weight of the dental preparation. Preferably, toothpastes contain from about 5 to about 60% by weight of abrasive with the abrasive particle size preferably ranging from about 2 microns to about 20 microns.

Suitable sudsing agents for use according to the present invention are those which are reasonably stable and form suds throughout a wide pH range and are acceptable for use in the oral cavity. Examples of some suitable sudsing agents include water-soluble salts of sulfonated monoglycerides of fatty acids having from about 10 to about 18 carbon atoms such as sodium coconut monoglyceride sulfonate; water-soluble salts of fatty acid amines of taurine such as sodium N-methyl-N-palmitoyl tauride; water-soluble salts of fatty acid esters of isethionic acid such as the coconut acid ester of sodium isethionate; substantially saturated aliphatic acyl amides of saturated aliphatic monoamino carboxylic acid having from about 2 to about 6 carbon atoms and in which the acyl radical contains from about 12 to about 16 carbon atoms such as sodium N-lauroyl sarcosinate; and the polyoxyalkylene polyols such as the Pluronics from Wyandotte Corporation. Likewise, mixtures of the sudsing agents can be employed when desired. Generally, the sudsing agent, when present, is employed in amounts ranging from about 0.5 to about 5.0% by weight.

Moreover, when desired, flavoring agents can be included in the dental preparations employed according to the present invention and include such flavoring agents as oil of wintergreen, oil of peppermint, oil of anise, citrus flavors, and vanillin. Likewise, various sweetening agents such as, for example, saccharin, dextrose, mannitol, levulose, and sodium cyclamate can be employed when desired.

In certain of the compositions contemplated by the present invention, such as toothpaste, it is generally desirable to employ thickening agents, exemplary of which are hydroxyethyl cellulose, water-soluble salts of cellulose ethers, including sodium carboxymethyl cellulose and sodium carboxymethylhydroxyethyl cellulose, and natural gums such as gum karaya, gum arabic and gum tragacanth. In addition, colloidal magnesium aluminum silicate or finely divided silica such as silica aerogels and microfine precipitated silicas can be used as part of the thickening agent to further improve texture in such compositions as toothpastes. The thickening agents are generally employed in amounts from about 0.1 to about 15% by weight when utilized.

In addition, in certain of the dental preparations employed in the present invention, such as toothpastes, it may be desirable to include a humectant or a viscosity modifying material. Examples of some suitable humectants include nontoxic polyhydric alcohols such as glycerin, sorbitol, mannitol, propylene glycol, polyethylene glycol, polypropylene glycol, and mixtures thereof. The humectants are generally present in amounts up to about 40% by weight of the dental preparation.

A typical toothpaste of the present invention can contain the amidoamine oxide in an amount sufficient to retard plaque and pellicle formation, from about 5 to about 60% by weight of an abrasive polishing agent, from about 0.5 to about 5% by weight of a sudsing agent, from about 0.1 to about 15% by weight of a thickening agent, and the balance being substantially water and humectants. A typical mouthwash composition suitable for practicing the present invention can contain the amidoamine oxide in an amount sufficient to retard pellicle and plaque formation, a sudsing agent, ethyl alcohol, humectant, sweetener, flavor, and water. A typical chewing gum composition useful for the present invention can contain the amidoamine oxide in an amount sufficient to retard pellicle and plaque formation, and a gum base. A prophylactic paste suitable for the present invention can include the amidoamine oxide in an amount sufficient to retard pellicle and plaque formation and pumice.

In addition, the present invention can be practiced by coating and impregnating dental floss or toothpicks with a composition containing the amidoamine oxides of the present invention. The coating operation can be carried out by any means will known for coating and impregnating fibers such as by passing dental floss or toothpicks through an aqueous bath of the amidoamine oxides and then permitting the water to evaporate, e.g., by heating under vacuum.

The following nonlimiting examples are provided to further demonstrate the present invention.

EXAMPLE 1

Part A

A set of three extracted human teeth without the roots is mounted on a plastic strip. The teeth are then swabbed with human saliva using a sterile Dacron swab and allowed to dry for about 15 minutes. The strip is then placed in a petri dish and covered with about 200 ml of an aqueous solution of about 2% trypticase and about 4% sucrose. Each dish is then inoculated with an additional 1 ml of human saliva and then incubated at about 37° C for about 24 hours.

Next, the set of teeth is removed from the media, dried, and then dipped into a 0.5% aqueous solution of FD & C RED No. 3 to visually disclose the plaque. The strip is then rinsed under tap water.

The teeth show heavy plaque growth. The teeth are then brushed with an electric toothbrush fitted with a soft nylon brush carrying a composition containing about 10% by weight dimethylaminopropyl tallow amide N-oxide available under the trade designation Tegamine HTG oxide

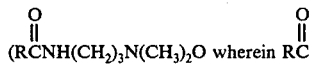
(RCNH(CH$_2$)$_3$N(CH$_3$)$_2$O wherein RC is from tallow acids), and the remainder being distilled water, until all of the red disclosed plaque is removed and are then rinsed.

After brushing, the teeth are rinsed with water and are then again swabbed with human saliva, placed in a petri dish covered with the trypticase-sucrose media, which is then inoculated with an additional 1 ml of saliva and incubated for about 24 hours at about 37° C. At the end of the 24 hours, the set of teeth is removed from the media, dried, and dipped into a 0.5% FD & C RED No. 3 solution for about 60 seconds to visually disclose the presence of plaque and is then rinsed under tap water. No plaque growth is observed on the teeth brushed with the Tegamine HTG oxide. The dimethylaminopropyl tallow amide N-oxide completely inhibited the deposition of dental plaque on the teeth.

COMPARISON

Part B

The general procedure of Part A of this example is repeated except that the set of teeth employed is brushed with water until all of the red disclosed plaque is removed. The results after the second 24-hour incubation show heavy plaque growth on the teeth brushed with water.

EXAMPLE 2

Example 1A is repeated except that the set of teeth employed is brushed with a composition of about 10% by weight of diethylaminopropylpalmitamide N-oxide

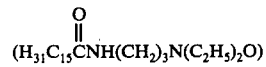
(H$_{31}$C$_{15}$CNH(CH$_2$)$_3$N(C$_2$H$_5$)$_2$O)

and the remainder being distilled water.

The diethylaminopropylpalmitamide N-oxide employed in this example is obtained by the following procedure.

About 40 cc of toluene and about 13 grams of diethylaminopropylamine are added to a 500 ml round bottom flask equipped with a Dean Stark (10 ml) water trap and a 300 mm reflux condenser. The mixture is refluxed for about 4 hours to remove the water from the toluene. After this a drop of concentrated HCl and a drop of concentrated H$_2$SO$_4$ are added. Next about 13 grams of palmitic acid (Emersol 144) are refluxed for about 38 hours. After this, the flask is allowed to cool and then is attached to a rotovacuum for several hours to remove all of the toluene. The remaining precipitate is redissolved in warm ethyl acetate, cooled, and filtered. It is again dissolved in warm ethyl acetate, cooled and filtered.

About 4.8 grams of the product (diethylaminopropylpalmitamide) and about 30 grams of distilled water are added to a 100 ml beaker. The beaker is then placed in a water bath at about 55°–70° C. The mixture is stirred until a uniform mixture is obtained. At five separate intervals of about 10 minutes each, 1 gram of 30% aqueous solution of H$_2$O$_2$ is added at each interval with agitation while maintaining the temperature of the uniform mixture at about 55°–70° C. A total of 5 grams of 30% aqueous solution of H$_2$O$_2$ are added. After the last addition of the aqueous H$_2$O$_2$ solution, the mixture is agitated at about 55°–70° C for about 60 minutes. The product is then dried by placing the reaction mixture in a vacuum oven for about 2 days. An infrared scan of the product indicates that it is the desired diethylaminopropylpalmitamide N-oxide.

The results of the test after the second 24-hour incubation period indicate that diethylaminopropylpalmitamide N-oxide prevents the formation of plaque and pellicle on the teeth.

EXAMPLE 3

Example 1A is repeated except that the set of teeth employed is brushed with a composition of about 1% by weight of dimethylaminopropyl oleamide N-oxide

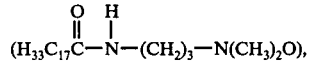
(H$_{33}$C$_{17}$C—N—(CH$_2$)$_3$—N(CH$_3$)$_2$O), and the remainder being distilled water.

The results of the test after the second 24-hour incubation period indicate that dimethylaminopropyl oleamide N-oxide prevents plaque and pellicle from forming on the teeth.

The dimethylaminopropyl oleamide N-oxide employed in this example is obtained by the following procedure:

About 5 grams of dimethylaminopropyl oleamide (Tegamine 0-13) and about 30 grams of distilled water are added to a 100 ml beaker. The beaker is then placed in a water bath at about 55°–70° C. The mixture is stirred until a uniform mixture is obtained. At 5 separate intervals of about 10 minutes each, 1 gram of 30% aqueous solution of H₂O₂ is added at each interval with agitation while maintaining the temperature of the uniform mixture at about 55°–70° C. A total of 5 grams of 30% aqueous solution of H₂O₂ are added. After the last addition of the aqueous H₂O₂ solution, the mixture is agitated at about 55°–70° C for about 30 minutes. The product is then dried by placing the reaction mixture in a vacuum oven for about 36 hours.

EXAMPLE 4

Example 1A is repeated except that the set of teeth employed is brushed with a composition of about 1% by weight of dimethylaminopropyl isostearamide N-oxide

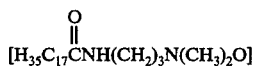

and the remainder being distilled water.

The results of the test after the second 24-hour incubation period indicate that dimethylaminopropyl isostearamide N-oxide prevents plaque and pellicle from forming on the teeth.

The dimethylaminopropyl isostearamide N-oxide employed in this example is prepared by the following procedure.

About 40 ml of toluene, about 10.5 grams of dimethylaminopropylamine, a drop of concentrated H₂SO₄, and 14.2 grams of isostearic acid are added to a 500 ml round bottom flask equipped with a Dean Stark (10 ml) water trap and a 300 mm reflux condenser. The reaction mass is refluxed for about 27 hours. After this, the flask is allowed to cool and then is attached to a rotovacuum for several hours to remove all of the toluene. The remaining precipitate is redissolved in warm ethyl acetate, cooled, and filtered. It is again dissolved in warm ethyl acetate, cooled and filtered whereby about 4 grams of product are obtained. An infrared scan of the product indicates that it is dimethylaminopropylisostearamide.

About 5.0 grams of the dimethylaminopropylisostearamide and about 30 grams of distilled water are added to a 150 ml beaker. The beaker is then placed in a water bath at about 55°–70° C. The mixture is stirred until a uniform mixture is obtained. At 5 separate intervals of about 10 minutes each, 1 gram of 30% aqueous solution of H₂O₂ is added at each interval with agitation while maintaining the temperature of the uniform mixture at about 55°–70° C. A total of 5 grams of 30% aqueous solution of H₂O₂ are added. After the last addition of the aqueous H₂O₂ solution, the mixture is agitated at about 55°–70° C for about 30 minutes. The product is then dried by placing the reaction mixture in a vacuum oven for several hours.

EXAMPLE 5

Example 1A is repeated except that the set of teeth employed in brushed with a composition of about 1% by weight of dimethylaminopropyl myristamide N-oxide

and the remainder being distilled water.

The results of the test after the second 24-hour incubation period indicate that dimethylaminopropyl myristamide N-oxide prevents plaque and pellicle from forming on the teeth.

The dimethylaminopropyl myristamide N-oxide employed in this example is prepared by the following procedure.

About 5.0 grams of dimethylaminopropyl myristamide and about 30 grams of distilled water are added to a 100 ml beaker. The beaker is then placed in a water bath at about 55°–70° C. The mixture is stirred until a uniform mixture is obtained. At 5 separate intervals of about 10 minutes each, 1 gram of 30% aqueous solution of H₂O₂ is added to each interval with agitation while maintaining the temperature of the uniform mixture at about 55°–70° C. A total of 5 grams of 30% aqueous solution of H₂O₂ are added. After the last addition of the aqueous H₂O₂ solution, the mixture is agitated at about 55°–70° C for about 30 minutes. The product is then dried by placing the reaction mixture in a vacuum oven for several days.

EXAMPLE 6

Example 1A is repeated except that the set of teeth employed is brushed with a composition of about 1% by weight of dimethylaminopropylpentadecanamide N-oxide

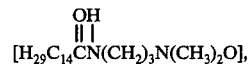

and the remainder being distilled water.

The results of the test after the second 24-hour incubation period indicate that dimethylaminopropylpentadecanamide N-oxide prevents plaque and pellicle from forming on the teeth.

The dimethylaminopropylpentadecanamide N-oxide employed in this example is prepared by the following procedure.

About 60 cc of toluene and about 5.1 grams of dimethylaminopropylamine are added to a 500 ml round bottom flask equipped with a Dean Stark (10 ml) water trap and a 300 mm reflux condenser. The mixture is refluxed for about 4 hours to remove the water from the toluene. After this a drop of concentrated HCl and a drop of concentrated H₂SO₄ are added. Next about 6 grams of pentadecanoic acid are added. The reaction mass is refluxed for about 21 hours. About 0.61 ml of water are collected. After this, the flask is allowed to cool and then is attached to a rotovacuum for several hours to remove all of the toluene. The remaining precipitate is redissolved in warm ethyl acetate, cooled, and filtered. It is again dissolved in warm ethyl acetate, cooled and filtered whereby very fine white crystals are obtained.

An infrared scan of the product indicates that it is dimethylaminopropylpentadecanamide.

About 2.8 grams of the dimethylaminopropylpentadecanamide prepared above and about 50 grams of distilled water are added to a 100 ml beaker. To this mixture is added 11.0 grams of 30% aqueous solution of hydrogen peroxide. The beaker is then placed in a water bath at about 90° C. The mixture is stirred for 1 hour, after which an additional 3.0 grams of $H_2O_2$ (30%) are added. A total of 14 grams of 30% aqueous solution of $H_2O_2$ are added. After the last addition of the aqueous $H_2O_2$ solution, the mixture is agitated at about 90° C for about 30 minutes.

The product is then dried by placing the reaction mixture in a vacuum oven for several days. An infrared scan of the product indicates that it is the desired dimethylaminopropylpentadecanamide N-oxide.

EXAMPLE 7

Example 1A is repeated except that the set of teeth employed is brushed with a composition of essentially all dimethylaminopropylcocoamide N-oxide (Ammonyx CDO). The results of the test after the second 24-hour incubation period indicates that the composition prevents plaque and pellicle from forming on the teeth.

However, compositions containing about 10% by weight of Ammonyx CDO and the remainder distilled water do not inhibit plaque and/or pellicle growth on the teeth. It is believed that these latter tests are negative since dimethylaminopropylcocoamide N-oxide contains only minor amounts of amine oxides within the scope of the present invention along with major quantities of amine oxide not within the scope of the present invention. Accordingly, when the dimethylaminopropylcocoamide N-oxide is diluted to concentrations found quite suitable for amine oxides within the scope of the present invention, the concentration of those amine oxides in the cocoamide amine oxide within the scope of this invention are no longer present in an amount effective to inhibit plaque and/or pellicle formation.

The results from using the diluted Ammonyx CDO compositions illustrate that compounds similar to those required according to the present invention, except that R contains carbon atoms outside of the range set forth herein, do not retard plaque and pellicle deposition as achieved by the present invention.

EXAMPLE 8

Example 1A is repeated except that the set of teeth employed is brushed with a composition of about 10% by weight of dimethylaminopropylpalmitamide N-oxide available under the trade designation Tegamine P Oxide

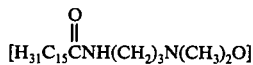

and the remainder being distilled water.

The results of the test after the second 24-hour incubation period indicate that dimethylaminopropylpalmitamide N-oxide prevents the formation of plaque and pellicle on the teeth.

EXAMPLE 9

A set of three extracted human teeth without the roots is mounted on a polymethylmethacrylate plastic strip of about 1 × 3 inches. A drop of human saliva is applied to each tooth and allowed to dry. The set of teeth is then placed in a petri dish and covered with about 200 ml of an aqueous solution of about 2% trypticase and about 4% sucrose. The dish is then inoculated with an additional 1 ml of human saliva and then incubated at about 37° C for about 24 hours.

Next, the set of teeth is removed from the media, rinsed, and then dipped into a 0.5% aqueous solution of FD & C RED No. 3 to visually disclose the plaque.

The teeth show heavy plaque growth. The teeth are then brushed with water using an electric toothbrush fitted with a soft nylon brush until all of the red disclosed plaque and/or pellicle is removed.

The teeth are then swabbed with human saliva, placed in a petri dish covered with about 200 ml of the trypticase-sucrose media and about 0.1 ml of a composition containing about 1% of dimethylaminopropylstearamide N-oxide

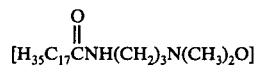

and the remainder being distilled water.

The contents of the dish are then inoculated with an additional 1 ml of saliva and incubated for about 24 hours at about 37° C. At the end of the 24 hours, the set of teeth is removed from the media, dried, and dipped into a 0.5% FD & C RED No. 3 solution for about 60 seconds to visually disclose the pesence of pellicle and plaque and is then rinsed under tap water. Light pellicle and/or plaque growth are observed on the teeth and strip contacted with the dimethylaminopropyl stearamide N-oxide.

The dimethylaminopropyl stearamide N-oxide employed in this example is prepared by the following procedure.

About 5 grams of dimethylaminopropyl stearamide (available under the trade designation Tegamine S-13) and about 30 ml of water are added to a beaker. The beaker is then placed in a heated water bath of about 70°–90° C. To this mixture is added about 5 grams of a 30% aqueous solution of hydrogen peroxide over a 40 minute period (i.e., about 1 gram of solution every 10 minutes). The mixture is stirred with heating at about 70°–90° C for an additional 30 minutes. To facilitate stirring an additional 10 ml of $H_2O$ was added during the reaction to the reaction mixture to replace water which evaporated during the reaction. The product is then dried by placing the reaction in a vacuum oven for about 48 hours. The product is a white powder having a melting point of 88°–94° C.

In all of the above examples, cleaned sets of teeth and new toothbrushes are employed for the brushings, respectively. The teeth are cleaned by thorough washing, after which they are placed in a petri dish covered with the trypticase-sucrose solution and incubated for the first 24-hour incubation period to verify that the teeth will support growth of plaque thereon.

What is claimed is:

1. A method for retarding pellicle and plaque formation which comprises intermittently contacting sites of plaque formation and growth with a preparation comprising an amount sufficient to retard pellicle and plaque formation of at least one compound of the formula:

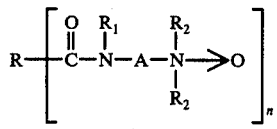

wherein R is a monovalent or divalent hydrocarbyl group containing at least 13 carbon atoms, *n* is one when R is monovalent and is 2 when R is divalent; $R_1$ is H or an alkyl group containing from 1 to about 3 carbon atoms; A is a divalent hydrocarbon bridge containing from 1 to about 6 carbon atoms; and each $R_2$ individually is an alkyl group containing from 1 to about 5 carbon atoms; or both $R_2$ groups are interconnected to form a heterocyclic ring with the N atom to which they are attached and contain 5 to 6 members in the ring; and wherein said heterocyclic ring is selected from the group consisting of morpholinyl, piperidinyl, pyrrolidinyl, and piperazinyl.

2. The method of claim 1 wherein R is a monovalent hydrocarbyl group.

3. The method of claim 1 wherein R is an aliphatic hydrocarbon group.

4. The method of claim 1 wherein R contains from 13 to about 21 carbon atoms.

5. The method of claim 1 wherein R contains from 15 to about 21 carbon atoms.

6. The method of claim 1 wherein R contains from 15 to about 17 carbon atoms.

7. The method of claim 1 wherein $R_1$ is hydrogen or methyl

8. The method of claim 1 wherein $R_1$ is H.

9. The method of claim 1 wherein A is an alkylene or alkylidene group.

10. The method of claim 1 wherein A is an alkylene or alkylidene group containing 1 to 3 carbon atoms.

11. The method of claim 1 wherein each $R_2$ individually is an alkyl group containing from 1 to about 5 carbon atoms.

12. The method of claim 1 wherein each $R_2$ individually is an alkyl group containing from 1-3 carbon atoms.

13. The method of claim 1 wherein $R_2$ is methyl.

14. The method of claim 1 wherein $R_2$ is ethyl.

15. The method of claim 1 wherein $R_1$ is H, A is an alkylene or alkylidene group containing from 1 to 3 carbon atoms and each $R_2$ group individually is methyl or ethyl.

16. The method of claim 1 wherein R is an aliphatic hydrocarbon group.

17. The method of claim 1 wherein said compound is dimethylaminopropyl tallow amide N-oxide.

18. The method of claim 1 wherein said compound is diethylaminopropylpalmitamide N-oxide or dimethylaminopropylpalmitamide N-oxide or mixtures thereof.

19. The method of claim 1 wherein said compound is dimethylaminopropyloleamide N-oxide.

20. The method of claim 1 wherein said compound is dimethylaminopropyl stearamide N-oxide.

21. The method of claim 1 wherein said compound is dimethylaminopropyl myristamide N-oxide.

22. The method of claim 1 wherein said compound is dimethylaminopropylpentadecanamide N-oxide.

23. The method of claim 1 which comprises intermittently contacting the oral cavity.

24. The method of claim 1 wherein the preparation contains at least about 0.1% by weight of the compound.

25. The method of claim 1 wherein the preparation contains from about 1 to about 25% by weight of the compound.

26. The method of claim 1 wherein said preparation also contains from about 5 to about 60% by weight of an abrasive polishing agent; from about 0.5 to about 5% by weight of a sudsing agent; from about 0.1 to about 15% by weight of a thickening agent; water and humectants.

27. The method of claim 1 wherein said preparation is in the form of a mouthwash and further includes a sudsing agent, ethyl alcohol, a humectant, sweetener, flavoring agent, and water.

28. The method of claim 1 wherein said preparation is in the form of a prophylactic paste which further includes pumice.

29. The method of claim 1 wherein said preparation contains water.

30. A dental preparation retarding pellicle and plaque formation which comprises an amount sufficient to retard pellicle and plaque formation of at least one compound of the formula:

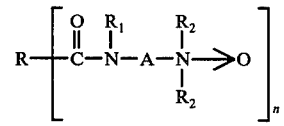

wherein R is a monovalent or divalent hydrocarbon group containing at least 13 carbon atoms, *n* is one when R is monovalent and is 2 when R is divalent, $R_1$ is H or an alkyl group containing from 1 to about 3 carbon atoms, A is a divalent hydrocarbon bridge containing from 1 to about 6 carbon atoms, each $R_2$ individually is an alkyl group containing from 1 to about 5 carbon atoms, or both $R_2$ groups are interconnected to form a heterocyclic ring with the N atom to which they are attached and contain 5 to 6 members in the ring, and being selected from the group consisting of morpholinyl, piperidinyl, pyrrolidinyl, and piperazinyl; from about 5 to about 50% by weight of an abrasive polishing agent; from about 0.5 to about 5% by weight of a sudsing agent; from about 0.1 to about 15% by weight of a thickening agent; and water.

31. A dental preparation in the form of a mouthwash for retarding pellicle and plaque formation which comprises an amount sufficient to retard pellicle and plaque formation of at least one compound of the formula:

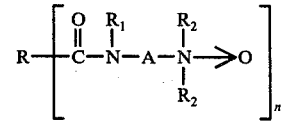

wherein R is a monovalent or divalent hydrocarbyl group containing at least 13 carbon atoms; *n* is one when R is monovalent and is 2 when R is divalent; $R_1$ is H or an alkyl group containing from 1 to about 3 carbon atoms; A is a divalent hydrocarbon bridge containing from 1 to about 6 carbon atoms; each $R_2$ individually is an alkyl group containing from 1 to about 5 carbon atoms; or both $R_2$ groups are interconnected to form a heterocyclic ring with the N atom to which they are attached and contain 5 to 6 members in the ring; a sudsing agent; ethyl alcohol; a humectant; sweetner; flavoring agent; and water.

32. A dental preparation in the form of a prophylactic paste for retarding pellicle and plaque formation which comprises an amount sufficient to retard pellicle and plaque formation of at least one compound of the formula:

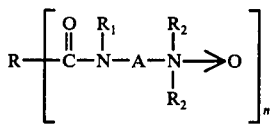

wherein R is a monovalent or divalent hydrocarbyl group containing at least 13 carbon atoms; $n$ is one when R is monovalent and is 2 when R is divalent; $R_1$ is H or an alkyl group containing from 1 to about 3 carbon atoms; A is a divalent hydrocarbon bridge containing from 1 to about 6 carbon atoms; each $R_2$ individually is an alkyl group containing from 1 to about 5 carbon atoms; or both $R_2$ groups are interconnected to form a heterocyclic ring with the N atom to which they are attached and contain 5 to 6 members in the ring, and being selected from the group consisting of morpholinyl, piperidinyl, pyrrolidinyl, and piperazinyl; and pumice.

33. A dental preparation for retarding pellicle and plaque formation which comprises an amount sufficient to retard pellicle and plaque formation of at least one compound of the formula:

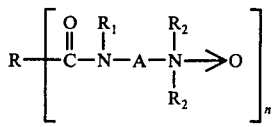

wherein R is a monovalent or divalent hydrocarbyl group containing at least 13 carbon atoms; $n$ is one when R is monovalent and is 2 when R is divalent; $R_1$ is H or an alkyl group containing from 1 to about 3 carbon atoms; A is a divalent hydrocarbon bridge containing from 1 to about 6 carbon atoms; each $R_2$ individually is an alkyl group containing from 1 to about 5 carbon atoms; or both $R_2$ groups are interconnected to form a heterocyclic ring with the N atom to which they are attached and contain 5 to 6 members in the ring; and being selected from the group consisting of morpholinyl, piperidinyl, pyrrolidinyl, and piperazinyl; water; and ethyl alcohol.

34. The method of claim 1 wherein said preparation includes hydrated alumina.

35. The method of claim 1 wherein said preparation includes polyoxyalkylene polyol.

* * * * *